United States Patent
Johnston et al.

(10) Patent No.: US 8,853,469 B2
(45) Date of Patent: Oct. 7, 2014

(54) COMBINED COLUMN FOR SEPARATING PRODUCTS OF DIFFERENT HYDROGENATION REACTORS

(71) Applicant: Celanese International Corporation, Irving, TX (US)

(72) Inventors: Victor J. Johnston, Houston, TX (US); David Lee, Seabrook, TX (US); Mark O. Scates, Houston, TX (US); R. Jay Warner, Houston, TX (US); Heiko Weiner, Pasadena, TX (US); Radmila Wollrab, Pasadena, TX (US); Zhenhua Zhou, Houston, TX (US); Emily Duff, League City, TX (US); Andrew Shuff, League City, TX (US)

(73) Assignee: Celanese International Corporation, Irving, TX (US)

( * ) Notice: Subject to any disclaimer, the term of this patent is extended or adjusted under 35 U.S.C. 154(b) by 0 days.

(21) Appl. No.: 13/681,923

(22) Filed: Nov. 20, 2012

(65) Prior Publication Data
US 2014/0142351 A1 May 22, 2014

(51) Int. Cl.
C07C 27/04 (2006.01)
C07C 29/147 (2006.01)
C07C 29/84 (2006.01)

(52) U.S. Cl.
CPC ..................... *C07C 29/84* (2013.01)
USPC .......................... 568/885; 560/265

(58) Field of Classification Search
None
See application file for complete search history.

(56) References Cited

U.S. PATENT DOCUMENTS

| | | |
|---|---|---|
| 1,892,742 A | 1/1933 | Walter et al. |
| 2,591,672 A | 4/1952 | Catterall |
| 2,607,719 A | 8/1952 | Eliot et al. |
| 2,607,807 A | 8/1952 | Ford |
| 2,715,604 A | 8/1955 | Weaver, Jr. |
| 2,744,939 A | 5/1956 | Kennel |
| 2,801,209 A | 7/1957 | Muller et al. |
| 2,859,241 A | 11/1958 | Schnizer |
| 3,408,267 A | 10/1968 | Miller et al. |
| 3,445,345 A | 5/1969 | Katzen et al. |
| 3,466,334 A | 9/1969 | Young et al. |
| 3,925,490 A | 12/1975 | Reich et al. |
| 4,007,130 A | 2/1977 | Leach et al. |
| 4,308,131 A | 12/1981 | Bannon |
| 4,398,039 A | 8/1983 | Pesa et al. |
| 4,422,903 A | 12/1983 | Messick et al. |
| 4,426,541 A | 1/1984 | King |
| 4,451,677 A | 5/1984 | Bradley et al. |
| 4,455,198 A | 6/1984 | Zudkevitch et al. |
| 4,492,808 A | 1/1985 | Hagen et al. |
| 4,514,515 A | 4/1985 | Travers et al. |
| 4,520,213 A | 5/1985 | Victor |

(Continued)

FOREIGN PATENT DOCUMENTS

| | | |
|---|---|---|
| CN | 1944374 | 4/2007 |
| CN | 201768393 | 3/2011 |

(Continued)

*Primary Examiner* — Jafar Parsa
*Assistant Examiner* — Medhanit Bahta (57) ABSTRACT

Recovery of ethanol from a crude product comprising ethyl acetate obtained from the hydrogenation of acetic acid. The crude product is separated to form an organic stream that may be subjected to hydrogenolysis to form ethanol. The organic phase may comprise ethyl acetate is reacted via hydrogenolysis form ethanol that may be directly or indirectly fed to the separation zone or the hydrogenation reactor.

20 Claims, 2 Drawing Sheets

(56) References Cited

U.S. PATENT DOCUMENTS

| | | | |
|---|---|---|---|
| 4,544,511 | A | 10/1985 | Isshiki et al. |
| 4,611,085 | A | 9/1986 | Kitson |
| 4,613,700 | A | 9/1986 | Maki et al. |
| 4,629,711 | A | 12/1986 | Erpenbach et al. |
| 4,737,318 | A | 4/1988 | Ichino et al. |
| 4,762,817 | A | 8/1988 | Logsdon et al. |
| 4,777,303 | A | 10/1988 | Kitson et al. |
| 4,842,693 | A | 6/1989 | Wheldon |
| 4,843,170 | A | 6/1989 | Isshiki et al. |
| 4,978,778 | A | 12/1990 | Isshiki et al. |
| 5,008,235 | A | 4/1991 | Wegman et al. |
| 5,061,671 | A | 10/1991 | Kitson et al. |
| 5,137,861 | A | 8/1992 | Shih et al. |
| 5,196,601 | A | 3/1993 | Kitsuki et al. |
| 5,206,434 | A | 4/1993 | Scates et al. |
| 5,220,020 | A | 6/1993 | Buchwald et al. |
| 5,254,758 | A | 10/1993 | Hiles et al. |
| 5,292,704 | A | 3/1994 | Lester |
| 5,475,144 | A | 12/1995 | Watson et al. |
| 5,502,248 | A | 3/1996 | Funk et al. |
| 5,585,523 | A | 12/1996 | Weiguny et al. |
| 6,114,571 | A | 9/2000 | Abel et al. |
| 6,399,812 | B1 | 6/2002 | Yan et al. |
| 6,462,244 | B1 | 10/2002 | Huang et al. |
| 6,509,290 | B1 | 1/2003 | Vaughn et al. |
| 6,657,078 | B2 | 12/2003 | Scates et al. |
| 6,696,596 | B1 | 2/2004 | Herzog et al. |
| 6,768,021 | B2 | 7/2004 | Horan et al. |
| 6,809,217 | B1 | 10/2004 | Colley et al. |
| 6,812,372 | B2 | 11/2004 | Janssen et al. |
| 6,933,414 | B1 | 8/2005 | Stauffer |
| 7,084,312 | B1 | 8/2006 | Huber et al. |
| 7,361,794 | B2 | 4/2008 | Grosso |
| 7,375,049 | B2 | 5/2008 | Hayes et al. |
| 7,518,014 | B2 | 4/2009 | Kimmich et al. |
| 7,572,353 | B1 | 8/2009 | Vander et al. |
| 7,585,339 | B2 | 9/2009 | Dahl et al. |
| 7,601,865 | B2 | 10/2009 | Verser et al. |
| 7,667,068 | B2 | 2/2010 | Miller et al. |
| 7,692,040 | B2 | 4/2010 | Key et al. |
| 7,744,727 | B2 | 6/2010 | Blum et al. |
| 7,790,920 | B2 | 9/2010 | Brtko et al. |
| 7,816,565 | B2 | 10/2010 | Johnston et al. |
| 7,847,134 | B2 | 12/2010 | Lee et al. |
| 7,888,082 | B2 | 2/2011 | Verser et al. |
| 7,902,397 | B2 | 3/2011 | Shaver |
| 7,947,746 | B2 | 5/2011 | Daniel et al. |
| 7,964,379 | B2 | 6/2011 | Verser et al. |
| 8,002,953 | B2 | 8/2011 | Lee et al. |
| 8,053,610 | B2 | 11/2011 | Kikuchi et al. |
| 8,062,482 | B2 | 11/2011 | Warner |
| 8,071,389 | B2 | 12/2011 | Weck et al. |
| 8,080,693 | B2 | 12/2011 | Chornet et al. |
| 8,128,826 | B2 | 3/2012 | Plante et al. |
| 8,143,444 | B2 | 3/2012 | Mariansky et al. |
| 8,211,821 | B2 | 7/2012 | Weiner et al. |
| 8,299,132 | B2 | 10/2012 | Gracey et al. |
| 8,299,133 | B2 | 10/2012 | Gracey et al. |
| 8,304,586 | B2 | 11/2012 | Jevtic et al. |
| 2001/0027172 | A1 | 10/2001 | Moore et al. |
| 2004/0242917 | A1 | 12/2004 | Inui et al. |
| 2007/0238605 | A1 | 10/2007 | Strehlau et al. |
| 2008/0207953 | A1 | 8/2008 | Houssin et al. |
| 2009/0209786 | A1 | 8/2009 | Scates et al. |
| 2011/0004034 | A1 | 1/2011 | Daniel et al. |
| 2011/0046421 | A1 | 2/2011 | Daniel et al. |
| 2011/0060169 | A1 | 3/2011 | Kaizik et al. |
| 2011/0098501 | A1* | 4/2011 | Johnston et al. ............... 560/265 |
| 2011/0190532 | A1* | 8/2011 | Johnston et al. ............... 560/248 |
| 2011/0224462 | A1 | 9/2011 | Ditzel et al. |
| 2011/0257442 | A1 | 10/2011 | Horton et al. |
| 2012/0010446 | A1 | 1/2012 | Warner et al. |
| 2012/0046501 | A1 | 2/2012 | Warner et al. |

FOREIGN PATENT DOCUMENTS

| | | |
|---|---|---|
| EP | 0087870 | 9/1983 |
| EP | 0108437 | 5/1984 |
| EP | 0175558 | 3/1986 |
| GB | 1559540 | 1/1980 |
| GB | 2053915 | 2/1981 |
| JP | 61-28181 | 2/1986 |
| JP | 6-116182 | 4/1994 |
| JP | 2000-178487 | 6/2000 |
| WO | WO 82/03854 | 11/1982 |
| WO | WO 2005/102520 | 11/2005 |
| WO | WO 2009/009320 | 1/2009 |
| WO | WO 2009/009322 | 1/2009 |
| WO | WO 2009/009323 | 1/2009 |
| WO | WO 2009/063176 | 5/2009 |
| WO | WO 2009063176 A1 * | 5/2009 |
| WO | WO 2012/148510 | 11/2012 |

* cited by examiner

COMBINED COLUMN FOR SEPARATING PRODUCTS OF DIFFERENT HYDROGENATION REACTORS

FIELD OF THE INVENTION

The present invention relates generally to processes for introducing the products from at least two different hydrogenation reactors into a single combined column. The combined column may yield a feed stream for at least one of the hydrogenation reactors. The process using the combined column may be useful in producing alcohols, such as ethanol.

BACKGROUND OF THE INVENTION

Ethanol for industrial use is conventionally produced from petrochemical feed stocks, such as oil, natural gas, or coal, from feed stock intermediates, such as syngas, or from starchy materials or cellulosic materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulosic material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition when conversion is incomplete, unreacted acid remains in the crude product, which must be removed to recover ethanol.

EP 2060555 describes a process for producing ethanol where a carbonaceous feedstock is converted to synthesis gas which is converted to ethanoic acid, which is then esterified and which is then hydrogenated to produce ethanol. U.S. Pat. No. 7,947,746 and US Pub. No. 2011/0224462 also describe a similar process where the esters produced from esterification are fed to the alcohol synthesis reactor used to produce ethanol and methanol.

WO 2009/063176 described a process for the production of ethanol from a carbonaceous feedstock, wherein the carbonaceous feedstock is first converted to synthesis gas which is then converted to ethanoic acid, which is then subject to a two stage hydrogenation process by which at least a part of the ethanoic acid is converted by a primary hydrogenation process to ethyl ethanoate, which ethyl ethanoate is converted by a secondary hydrogenation process to product ethanol.

US Pub. Nos. 2012/0010446 and 2012/0046501 describe the recovery of ethanol from a crude product obtained from the hydrogenation of acetic acid and by reacting a portion of the crude ethanol product or one or more derivative streams containing ethyl acetate obtained therefrom in the presence of hydrogen, via hydrogenolysis. The one or more derivative streams comprising ethyl acetate are reacted via hydrogenolysis to form ethanol that may be directly or indirectly fed to the separation zone or the hydrogenation reactor.

U.S. Pat. No. 6,399,812 teaches the production of aliphatic esters, R'COOR by reacting a corresponding alcohol, ROH, having carbon numbers of the alkyl groups, R' and R, between 0 and 9 and 1 and 10, respectively, with molecular oxygen and in the presence of a dual functional catalyst comprising metal on acidic solid support. The process may be used for production of ethyl acetate by conversion of ethanol.

Therefore, a need remains for improving the recovery of ethanol from crude products obtained by reducing alkanoic acids, such as acetic acid, and other carbonyl group-containing compounds.

SUMMARY OF THE INVENTION

In a first embodiment, the present invention is directed to a process for producing ethanol, comprising: hydrogenating acetic acid in the presence of a catalyst under conditions effective to form a crude product comprising ethyl acetate and ethanol, wherein ethyl acetate is present in a greater weight amount than ethanol; introducing at least a portion of the crude product at an inlet to a distillation column and obtaining an overhead that is condensed and collected, preferably in an overhead receiver; maintaining conditions, e.g., in the overhead receiver, to biphasically separate the overhead into an organic phase comprising ethyl acetate and an aqueous phase; feeding the aqueous phase to the distillation column above the inlet of the crude product to extract ethanol from ethyl acetate; feeding a secondary crude product formed by hydrogenolyzing at least a portion of the organic phase to the distillation column below the inlet of the crude product; and recovering ethanol from the residue of the distillation column. The secondary crude product is produced in a secondary reactor is different than the primary hydrogenation reactor for reacting acetic acid. The catalyst in the primary reactor may comprise a first metal selected from the group consisting of copper, iron, cobalt, nickel, ruthenium, rhodium, palladium, osmium, iridium, platinum, titanium, zinc and chromium. The catalyst in the primary reactor may further comprise a second metal selected from the group consisting of copper, tin, chromium, iron, cobalt, vanadium, palladium, platinum, lanthanum, cerium, manganese, ruthenium, gold and nickel, wherein the second metal is different from the first metal. The catalyst in the primary reactor may further comprise a support and at least one support modifier selected from the group consisting of oxides of Group IVB metals, oxides of Group VB metals, oxides of Group VIB metals, iron oxides, aluminum oxides, and mixtures thereof. The selectivity of acetic acid to ethyl acetate may be at least 50%.

In one embodiment, the organic phase may comprise at least 90 wt. % ethyl acetate. The distillation column may be an extractive distillation column wherein the extractive agent may be water. The residue may be separated in a second distillation column to form an ethanol stream and a water stream. The secondary crude product may comprise at least 5% more ethanol than the organic phase fed to a secondary reactor to form the hydrogenolysis product, i.e. secondary crude product. In some embodiments, the secondary crude product may be combined with the residue when the secondary crude product contains a relatively high ethanol concentration. The secondary reactor may contain a suitable hydrogenolysis catalyst, which may be different than the catalyst of the primary reactor.

Hydrogen may be fed with the organic phase to the secondary reactor to form the secondary crude product. The process may further comprise separating a vapor stream comprising hydrogen from the secondary crude product, and introducing the vapor stream to a secondary reactor or primary reactor for hydrogenating acetic acid.

In a second embodiment, the present invention is directed to a process for producing ethanol, comprising: providing a crude product comprising ethyl acetate and ethanol, wherein ethyl acetate is present in a greater weight amount than ethanol; introducing at least a portion of the crude product at an inlet to a distillation column and obtaining an overhead that is condensed and collected, preferably in an overhead receiver; maintaining conditions, e.g., in the overhead receiver, to biphasically separate the overhead into an organic phase comprising ethyl acetate and an aqueous phase; feeding the aqueous phase to the distillation column above the inlet of the crude product to extract ethanol from ethyl acetate; feeding a secondary crude product formed by hydrogenolyzing at least a portion of the organic phase to the distillation column below the inlet of the crude product; and recovering ethanol from the residue of the distillation column. The crude product may comprise from 5 to 40 wt. % ethanol and from 40 to 95 wt. % ethyl acetate. The secondary crude product is produced in a secondary reactor is different than the primary hydrogenation reactor for reacting acetic acid. The catalyst in the primary reactor may comprise a first metal selected from the group consisting of copper, iron, cobalt, nickel, ruthenium, rhodium, palladium, osmium, iridium, platinum, titanium, zinc and chromium. The catalyst in the primary reactor may further comprise a second metal selected from the group consisting of copper, tin, chromium, iron, cobalt, vanadium, palladium, platinum, lanthanum, cerium, manganese, ruthenium, gold and nickel, wherein the second metal is different from the first metal. The catalyst in the primary reactor may further comprise a support and at least one support modifier selected from the group consisting of oxides of Group IVB metals, oxides of Group VB metals, oxides of Group VIB metals, iron oxides, aluminum oxides, and mixtures thereof. The selectivity of acetic acid to ethyl acetate may be at least 50%.

In one embodiment, the organic phase may comprise at least 90 wt. % ethyl acetate. The distillation column may be an extractive distillation column wherein the extractive agent may be water. The residue may be separated in a second distillation column to form an ethanol stream and a water stream. The secondary crude product may comprise at least 5% more ethanol than the organic phase fed to a secondary reactor to form the hydrogenolysis product, i.e. secondary crude product. In some embodiments, the secondary crude product may be combined with the residue when the secondary crude product contains a relatively high ethanol concentration. The secondary reactor may contain a suitable hydrogenolysis catalyst, which may be different than the catalyst of the primary reactor.

Hydrogen may be fed with the organic phase to the secondary reactor to form the secondary crude product. The process may further comprise separating a vapor stream comprising hydrogen from the secondary crude product, and introducing the vapor stream to a secondary reactor or primary reactor for hydrogenating acetic acid.

In a third embodiment, the present invention is directed to a process for producing ethanol, comprising: hydrogenating acetic acid in the presence of a catalyst under conditions effective to form a crude product comprising ethanol, acetic acid, ethyl acetate and water, wherein ethyl acetate is present in a greater weight amount than ethanol; separating at least a portion of the first crude product in a distillation column to form an overhead comprising ethyl acetate and water and a residue comprising ethanol and water; biphasically separating the overhead to form an organic phase comprising ethyl acetate and an aqueous phase comprising water; reacting at least a portion of the organic phase in the presence of hydrogen to form a secondary crude product; and recovering ethanol. In some embodiments, recovering ethanol may comprise combining the secondary crude product with the first residue to recover ethanol. The aqueous phase may be returned to the first distillation column. The distillation column may be an extractive distillation column wherein the extractive agent may be water. The organic phase may comprise at least 90 wt. % ethyl acetate. The residue may be separated in a second distillation column to form an ethanol stream and a water stream. The secondary crude product may comprise at least 5 wt. % more ethanol than the at least a portion of the organic phase fed to a reactor for hydrogenating the organic phase. The organic phase may be reacted in the presence of a hydrogenolysis catalyst. The hydrogenolysis catalyst may be copper-based.

In a fourth embodiment, the present invention is directed to a process for producing ethanol, comprising: providing a first crude product comprising ethanol, acetic acid, ethyl acetate and water; separating at least a portion of the first crude product in a distillation column to form an overhead comprising ethyl acetate and water and a residue comprising ethanol and water; biphasically separating the overhead to form an organic phase comprising ethyl acetate and an aqueous phase comprising water; reacting at least a portion of the organic phase in the presence of hydrogen to form a secondary crude product; and combining the secondary crude product with the first residue to recover ethanol. The first crude product may comprise from 5 to 40 wt. % ethanol and from 40 to 95 wt. % ethyl acetate. The aqueous phase may be returned to the first distillation column. The distillation column may be an extractive distillation column wherein the extractive agent may be water. The organic phase may comprise at least 90 wt. % ethyl acetate. The residue may be separated in a second distillation column to form an ethanol stream and a water stream. The secondary crude product may comprise at least 5 wt. % more ethanol than the at least a portion of the organic phase fed to a reactor for hydrogenating the organic phase. The organic phase may be reacted in the presence of a hydrogenolysis catalyst. The hydrogenolysis catalyst may be copper-based.

BRIEF DESCRIPTION OF DRAWINGS

The invention may be more completely understood in consideration of the following detailed description of various embodiments of the invention in connection with the accompanying drawings, wherein like numerals designate similar parts.

DETAILED DESCRIPTION OF THE INVENTION

Introduction

In general the present invention is related to a combined column for separating crude products from two different hydrogenation reactors. The hydrogenation reactors may be different due to the type of feed streams, catalyst, reaction conditions and/or products. In one embodiment, at least one of the feed streams is fresh acetic acid. In another embodiment, at least one of the feed streams is separated from the combined column. Each crude product from the different hydrogenation reactors are introduced into the combined column. The overhead of the combined column is condensed and bi-phasically separated in an overhead receiver, such as a decanter. In one embodiment, the organic phase from the overhead receiver may be the feed stream to at least one of the hydrogenation reactors. Advantageously the combined column can maintain conditions in the overhead receiver to phase the overhead. The desired product, such as ethanol, is obtained from the residue of the combined column. Thus, advantageously, ethanol does not need to be boiled up in the combined column and this may reduce overall energy requirements.

In one embodiment, the combined column is useful for producing ethanol. The present invention relates generally to processes for forming ethanol in an ethanol production system wherein an organic phase comprising ethyl acetate is obtained from the combined column. At least a portion of the organic phase is reacted with hydrogen to form ethanol. The processes are particularly well-suited for ethanol production systems in which acetic acid is hydrogenated in the presence of a catalyst to form ethanol. The conversion of acetic acid is high, e.g. at least 90%, at least 95%, or at least 99%. At least 10% of the acetic acid is converted to ethyl acetate, e.g. at least 20%, at least 30% or at least 40%. Ethanol may also be produced when converting acetic acid, but it is preferred to use a catalyst that is more selective to ethyl acetate.

In one embodiment, the feed streams to the primary reactor and secondary reactor may comprise acetic acid, acetic anhydride, acetaldehyde, ethyl acetate, and mixtures thereof. Preferably, acetic acid is fed to one reactor and ethyl acetate is fed to the other reactor. The ethyl acetate may be obtained by reacting acetic acid. Either of these feed streams may be converted directly to ethanol. The reaction schemes for ethyl acetate and acetic acid are as follows:

(I)

(II)

In another embodiment, the primary reactor or the secondary reactor may convert acetic acid to ethyl acetate through hydrogenation as follows:

(III)

Although it is preferred to hydrogenate acetic acid to ethyl acetate, ethyl acetate may also be formed by esterifying acetic acid as follows:

(IV)

Reaction conditions in one of the hydrogenation reactors are maintained such that reactions III and IV are favored over II, and thus may achieve higher selectivities to ethyl acetate. Higher selectivities to ethyl acetate in the primary reactor are needed to maintain conditions in the overhead receiver to phase the organic phase.

The processes of the present invention beneficially may be used in applications for the recovery and/or purification of ethanol on an industrial scale. For example, various aspects of the present invention relate to processes for recovering and/or purifying ethanol produced by a process comprising hydrogenating acetic acid and ethyl acetate in the presence of a catalyst.

In one exemplary embodiment, the crude product from the primary reactor comprises ethyl acetate, ethanol and water. The crude product comprises less than 10 wt. % acetic acid, e.g., less than 5 wt. % or less than 1 wt. % acetic acid. As discussed herein, unreacted acetic acid may be separated from the crude product and recycled to the reactor. The crude product comprises more ethyl acetate than ethanol, on a weight basis. In some embodiments, the crude product comprises at least 5 wt. % ethanol, e.g. at least 10 wt. %, at least 20 wt. % or at least 30 wt. %, and at least 40 wt. % ethyl acetate, e.g., at least 45 wt. %, at least 50 wt. % or at least 55 wt. %. In terms of ranges, the crude product may comprise from 5 to 40 wt. % ethanol, e.g. from 5 to 35 wt. %, from 5 to 30 wt. % or from 5 to 25 wt. % and from 40 to 95 wt. % ethyl acetate, e.g., from 45 to 90 wt. %, from 50 to 85 wt. % or from 50 to 75 wt. %.

An additional esterification reactor may also be used to increase the ethyl acetate concentration, as desired. The esterification reaction may also further decrease the acetic acid concentration and thus reduce the separation requirements.

The crude product is fed to a combined column to form an overhead comprising ethyl acetate and a residue comprising ethanol. The overhead also comprises small amounts of ethanol and/or water, e.g., less than 10 wt. %, less than 5 wt. % or less than 1 wt. %. Preferably, the overhead does not comprise any acetic acid. The overhead is condensed and collected in an overhead receiver, where it is biphasically separated to form an organic phase and an aqueous phase. The organic phase preferably comprises a majority of ethyl acetate. In some embodiments, the organic phase comprises at least 90 wt. % ethyl acetate, e.g., at least 92 wt. %, at least 95 wt. %, or at least 99 wt. %. The aqueous phase comprises mainly water and may also comprise small amounts of ethanol, e.g., less than 10 wt. %, less than 5 wt. % or less than 1 wt. %.

The aqueous phase is fed to the distillation column above the inlet of the crude product. This feed location allows the water to flow down through the combined column and to extract ethanol from ethyl acetate. Although some ethanol is removed in the overhead, most of this ethanol is recovered by feeding the aqueous phase to the combined column. Ethanol recovery is maximized, and the process is more efficient because less ethanol passes through the secondary reactor.

In some embodiments, the combined column is an extractive distillation column. The extractive agent may be water from the aqueous phase. Although water may be obtained from an external source, it is less preferred because this introduces additional water that needs to be separated from the ethanol product.

The residue from the combined column comprises ethanol and water and may be separated in a secondary distillation column to form an ethanol stream and a water stream. Additionally, water from an ethanol/water separation column may be fed as the extractive agent either with the aqueous phase or separately.

Returning to the organic phase, at least a portion of the organic phase is fed to a secondary reactor to form a hydrogenolysis product. This hydrogenolysis product of the organic phase comprises more ethanol than ethyl acetate, on a weight basis. The hydrogen from the secondary reactor may be separated, such as in a knock out pot or flasher, and introduced to the primary reactor with the acetic acid. Without being bound by theory, the pressure of the secondary reactor may be higher than the primary reactor, which may reduce the compression requirements when returning the hydrogen to the primary reactor.

In the secondary reactor, the catalyst, also referred to as a hydrogenolysis catalyst, may be copper-based. Suitable hydrogenolysis catalysts include copper supported on silica or copper oxide supported on magnesia-silica, Raney copper catalysts, Group VIII supported catalysts, and catalysts as described below in connection with the hydrogenation process. Further catalysts are described in U.S. Pat. No. 5,198,592, and Claus, et al., "Selective Hydrogenolysis of methyl and ethyl acetate in the gas phase on copper and supported Group VIII metal catalysts," Applied Catalysts A: General, Vol. 79 (1991) pages 1-18, both of which are hereby incorporated by reference. In one embodiment, the catalyst in the secondary reactor may be different than the primary reactor.

The hydrogenolysis product of the organic phase, which is mainly ethanol, may be fed to the combined column below the inlet of the crude product from the primary reactor and ethanol may be recovered from the residue. In some embodiments, especially when conversion of ethyl acetate in the organic phase to ethanol is high, the hydrogenolysis product of the organic phase may be combined with the residue.

The hydrogenolysis product of the organic phase may comprise at least 5% more ethanol than the at least a portion of the organic phase fed to the second reactor, e.g., at least 10% more, at least 15% more or at least 20% more.

Hydrogenation Process

A. Acetic Acid Sources

1. Carbonylation

In one embodiment, the production of ethanol may be integrated with such methanol carbonylation processes. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Preferably, the carbonylation process is a low water, catalyzed, e.g., rhodium-catalyzed, carbonylation of methanol to acetic acid, as exemplified in U.S. Pat. No. 5,001,259, which is hereby incorporated by reference.

The carbonylation reaction may be conducted in a homogeneous catalytic reaction system comprising a reaction solvent, methanol and/or reactive derivatives thereof, a Group VIII catalyst, at least a finite concentration of water, and optionally an iodide salt. Exemplary rhodium catalysts are described in Michael Gauβ, et al., *Applied Homogeneous Catalysis with Organometallic Compounds: A Comprehensive Handbook in Two Volumes*, Chapter 2.1, p. 27-200, ($1^{st}$ ed., 1996). For additional detail regarding rhodium catalysis and iodide salt generation, see U.S. Pat. Nos. 5,001,259; 5,026,908; and 5,144,068, which are hereby incorporated by reference. The carbonylation of methanol utilizing iridium catalyst is well known and is generally described in U.S. Pat. Nos. 5,942,460; 5,932,764; 5,883,295; 5,877,348; 5,877,347 and 5,696,284, the entireties of which are hereby incorporated by reference.

A halogen co-catalyst/promoter is generally used in combination with the Group VIII metal catalyst component. Promoters and co-promoters may be used as part of the catalytic system of the present invention as described in U.S. Pat. No. 5,877,348, which is hereby incorporated by reference. Specific co-promoters are described in U.S. Pat. No. 6,627,770, which is incorporated herein by reference.

2. Direct from Syngas

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenolysis step may be supplied from syngas.

In some embodiments, some or all of the raw materials may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the ethyl acetate to form the crude reaction mixture may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

3. Fermentation to Acetic Acid

In another embodiment, the acetic acid used in the hydrogenation reaction may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Exemplary fermentation processes for forming acetic acid are disclosed in U.S. Pat. Nos. 6,509,180; 6,927, 048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

4. Acetic Acid Feed

The acetic acid feed stream that is fed to the hydrogenation step may also comprise other carboxylic acids and anhydrides, acetaldehyde, and acetone. In one aspect, the acetic acid feed stream comprises one or more of the compounds selected from the group consisting of acetic acid, propionic acid, acetic anhydride, acetaldehyde, ethyl acetate, diethyl acetal, and mixtures thereof. These other compounds may also be hydrogenated in the processes of the present invention. Water may also be present, generally in amounts of less than 10 wt. %, in the acetic acid feed.

B. Hydrogenation Reaction

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethyl acetate may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 350° C., from 250° C. to 325° C., or from 290° C. to 320° C. The pressure may range from 10 kPa to 5000 kPa, e.g., from 500 kPa to 3500 kPa, or from 1000 kPa to 3100 kPa. Higher pressures may be used to favor selectivity to ethyl acetate. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The hydrogenation of acetic acid to form ethyl acetate is preferably conducted in the presence of a hydrogenation catalyst. In one embodiment, the catalyst may favor ethyl acetate over other compounds, such as acetaldehyde or ethanol. Suitable catalysts include those described in U.S. Pat. No. 7,820, 852 and U.S. Pub. Nos. 2010/0121114; 2010/0197959; 2010/ 0197486; and 2011/0098501, the entire contents and disclosure of which is incorporated by reference. Specific catalyst formulations include: a) 1 wt. % platinum and 5 wt. % copper on high purity low surface area silica; b) 1 wt. % palladium and 5 wt. % cobalt on H-ZSM-5; c) 1 wt. % palladium and 5 wt. % cobalt on high purity low surface area silica; d) 5 wt. % copper and 5 wt. % chromium on high purity low surface area silica; e) 5 wt. % molybdenum carbide on high purity low surface area silica; f) 1 wt. % platinum and 5 wt. % molybdenum on titania; g) 1 wt. % palladium on high purity low surface area silica; 1 wt. % palladium and 5 wt. % molybdenum on H-ZSM-5; i) 1 wt. % nickel and 5 wt. % molybdenum on carbon; j) 1 wt. % platinum on titania; k) 1 wt. % palladium and 5 wt. % rhenium on titania; 1) 1 wt. % platinum and 5 wt. % molybdenum on carbon; m) 1 wt. % palladium and 5 wt. % zirconium on silica; n) 1 wt. % platinum and 5 wt. % copper on titania; o) 1 wt. % nickel and 5 wt. % rhenium on titania; p) 1 wt. % platinum and 5 wt. % molybdenum on silica; q) 1 wt. % palladium and 5 wt. % molybdenum on silica; and r) 5 wt. % copper and 5 wt. % zirconium on silica.

Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIIB, VIIB, VIII transition metals, a lanthanide metal, an actinide metal or a metal selected from any of Groups IIIA, IVA, VA, and VIA.

Preferred metal combinations may include nickel/copper, nickel/cobalt, platinum/copper, platinum/cobalt, palladium/ copper, palladium/cobalt, nickel/rhenium, platinum/rhenium, palladium/rhenium, nickel/tin, platinum/tin, palladium/tin, nickel/molybdenum, platinum/molybdenum, or palladium/molybdenum.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from nickel, platinum, and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from copper, cobalt, tin, and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

Molar ratios other than 1:1 may be preferred depending on the composition of the catalyst employed. For example, for platinum/tin catalysts, platinum to tin molar ratios less than 0.4:0.6, or greater than 0.6:0.4 are particularly preferred in order to form ethyl acetate from acetic acid at high selectivity, conversion and productivity. More preferably, the Pt/Sn ratio is greater than 0.65:0.35 or greater than 0.7:0.3, e.g., from 0.65:0.35 to 1:0.35 or from 0.7:0.3 to 1:0.3. Selectivity to ethyl acetate may be further improved by incorporating modified supports as described herein.

With rhenium/palladium catalysts, preferred rhenium to palladium molar ratios for forming ethyl acetate in terms of selectivity, conversion and production are less than 0.7:0.3 or greater than 0.85:0.15. A preferred Re/Pd ratio for producing ethyl acetate in the presence of a Re/Pd catalyst is from 0.2:0.8 to 0.4:0.6. Again, selectivity to ethyl acetate may be further improved by incorporating modified supports as described herein.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 to 7.5 wt. %, e.g., from 0.1 to 5 wt. %, or from 0.1 to 3 wt. %.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 wt. % to 99.9 wt. %, e.g., from 78 wt. % to 97 wt. %, or from 80 wt. % to 95 wt. %. In preferred embodiments that utilize a modified support, the support modifier is present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

In addition to the metal, the catalysts of the first embodiment further comprise a support, optionally a modified support. As will be appreciated by those of ordinary skill in the art, support materials are selected such that the catalyst system is suitably active, selective and robust under the process conditions employed for the formation of ethyl acetate or a mixture of ethyl acetate and ethanol. Suitable support materials may include, for example, stable metal oxide-based supports or ceramic-based supports as well as molecular sieves, such as zeolites. Examples of suitable support materials include without limitation, iron oxide, silica, alumina, silica/aluminas, titania, zirconia, magnesium oxide, calcium silicate, carbon, graphite, high surface area graphitized carbon, activated carbons, and mixtures thereof. Exemplary preferred supports are selected from the group consisting of silica/aluminas, titania, and zirconia.

The supports may further comprise a support modifier. A support modifier is added to the support and is not naturally present in the support. A support modifier adjusts effects of the acidity of the support material. The acid sites, e.g. Brønsted acid sites, on the support material may be adjusted by the support modifier, for example, to favor selectivity to ethyl acetate and mixtures of ethyl acetate during the hydrogenation of acetic acid. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference.

As indicated, the catalyst support may be modified with a support modifier. In some aspects, the support material is too basic or is not acidic enough for formation of ethyl acetate at high selectivity. In this case, the support may be modified with a support modifier that adjusts the support material by increasing the number or availability of acid sites by using a redox support modifier or an acidic support modifier. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, and $Bi_2O_3$.

Without being bound by theory, it is believed that an increase in acidity of the support may favor ethyl acetate formation. However, increasing acidity of the support may also form ethers and basic modifiers may be added to counteract the acidity of the support.

In some aspects, the support material may be undesirably too acidic for formation of ethyl acetate at high selectivity. In this case, the support material may be modified with a basic support modifier. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

In particular, the hydrogenation of acetic acid may achieve favorable conversion of acetic acid and favorable selectivity and productivity to ethyl acetate. For purposes of the present invention, the term "conversion" refers to the amount of acetic acid in the feed that is converted to a compound other than acetic acid. Conversion is expressed as a percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethyl acetate, we refer to the ethyl acetate selectivity as 60%. Preferably, the selectivity to ethyl acetate is at least 50%, e.g., at least 60% or at least 80%. The catalyst should general favor selectivity to ethyl acetate over ethanol. However, any ethanol that is produced with ethyl acetate may be separated in the combined column. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethyl acetate, formed during the hydrogenation based on the kilograms of catalyst used per hour. A productivity of at least 100 grams of ethyl acetate per kilogram of catalyst per hour, e.g., at least 400 grams of ethyl acetate per kilogram of catalyst per hour or at least 600 grams of ethyl acetate per kilogram of catalyst per hour, is preferred. In terms of ranges, the productivity preferably is from 100 to 3,000 grams of ethyl acetate per kilogram of catalyst per hour, e.g., from 400 to 2,500 grams of ethyl acetate per kilogram of catalyst per hour or from 600 to 2,000 grams of ethyl acetate per kilogram of catalyst per hour.

In various embodiments of the present invention, the reactor product produced by the primary reactor, before any subsequent processing, such as purification and separation, will typically comprise ethyl acetate, ethanol, water, and one or more organic impurities. Exemplary compositional ranges for the reactor product are provided in Table 1. The "others" identified in Table 1 may include, for example, esters, ethers, aldehydes, ketones, alkanes, and carbon dioxide.

TABLE 1

CRUDE PRODUCT COMPOSITIONS

| Component | Conc. (wt. %) | Conc. (wt. %) | Conc. (wt. %) | Conc. (wt. %) |
|---|---|---|---|---|
| Ethanol | 5 to 40 | 5 to 35 | 5 to 30 | 5 to 25 |
| Acetic Acid | 0 to 10 | 0.01 to 5 | 0.1 to 5 | 0.1 to 1 |
| Water | 5 to 40 | 5 to 30 | 10 to 30 | 10 to 26 |
| Ethyl Acetate | 40 to 95 | 45 to 90 | 50 to 85 | 50 to 75 |
| Acetaldehyde | 0 to 10 | 0 to 3 | 0.1 to 3 | 0.2 to 2 |
| Others | 0.1 to 10 | 0.1 to 6 | 0.1 to 4 | — |

As indicated above, the hydrogenation process preferably forms primarily ethanol and ethyl acetate. In other embodiments, the catalyst selected for hydrogenating acetic acid may favor the formation of ethyl acetate, i.e., has a greater selectivity for ethyl acetate than for ethanol, and particularly may favor formation of mixtures of ethanol and ethyl acetate. In these embodiments, the crude product may have more ethyl acetate, on a weight basis, than the crude product as described above in Table 1. The processes of the present invention advantageously can tolerate increased formation of ethyl acetate since ultimately the ethyl acetate will be converted to ethanol in the hydrogenolysis step.

In one embodiment, the crude product may comprise acetic acid in an amount less than 20 wt. %, e.g., of less than 15 wt. %, less than 10 wt. % or less than 5 wt. %. In embodiments having lower amounts of acetic acid, the conversion of acetic acid is preferably greater than 75%, e.g., greater than 85% or greater than 90%. In addition, the selectivity to ethanol may also be preferably high, and is preferably greater than 75%, e.g., greater than 85% or greater than 90%.

Purification System

Figure 1:
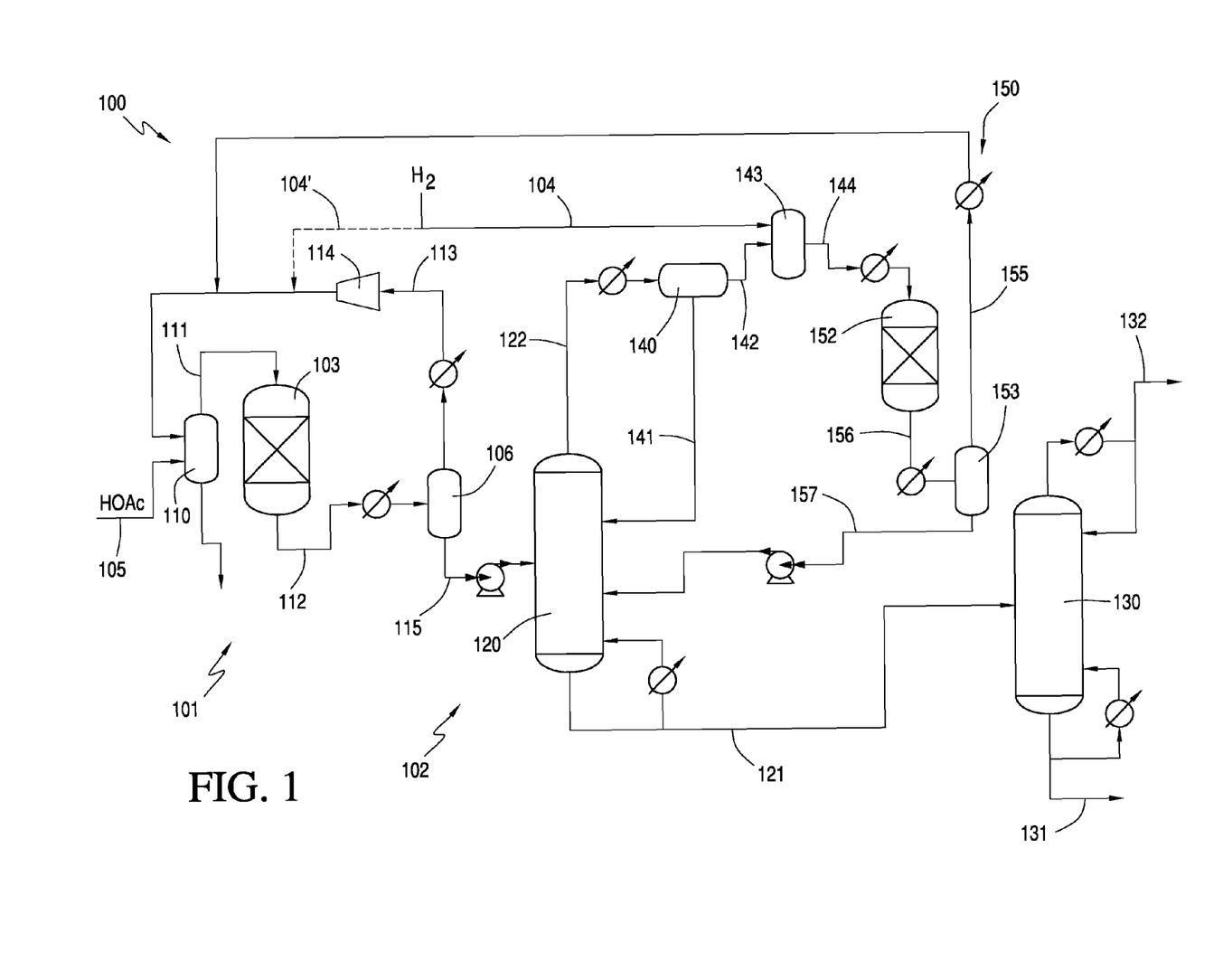
FIG. 1 is a schematic diagram of an ethanol production system in accordance with one embodiment of the present invention.
Figure 2:
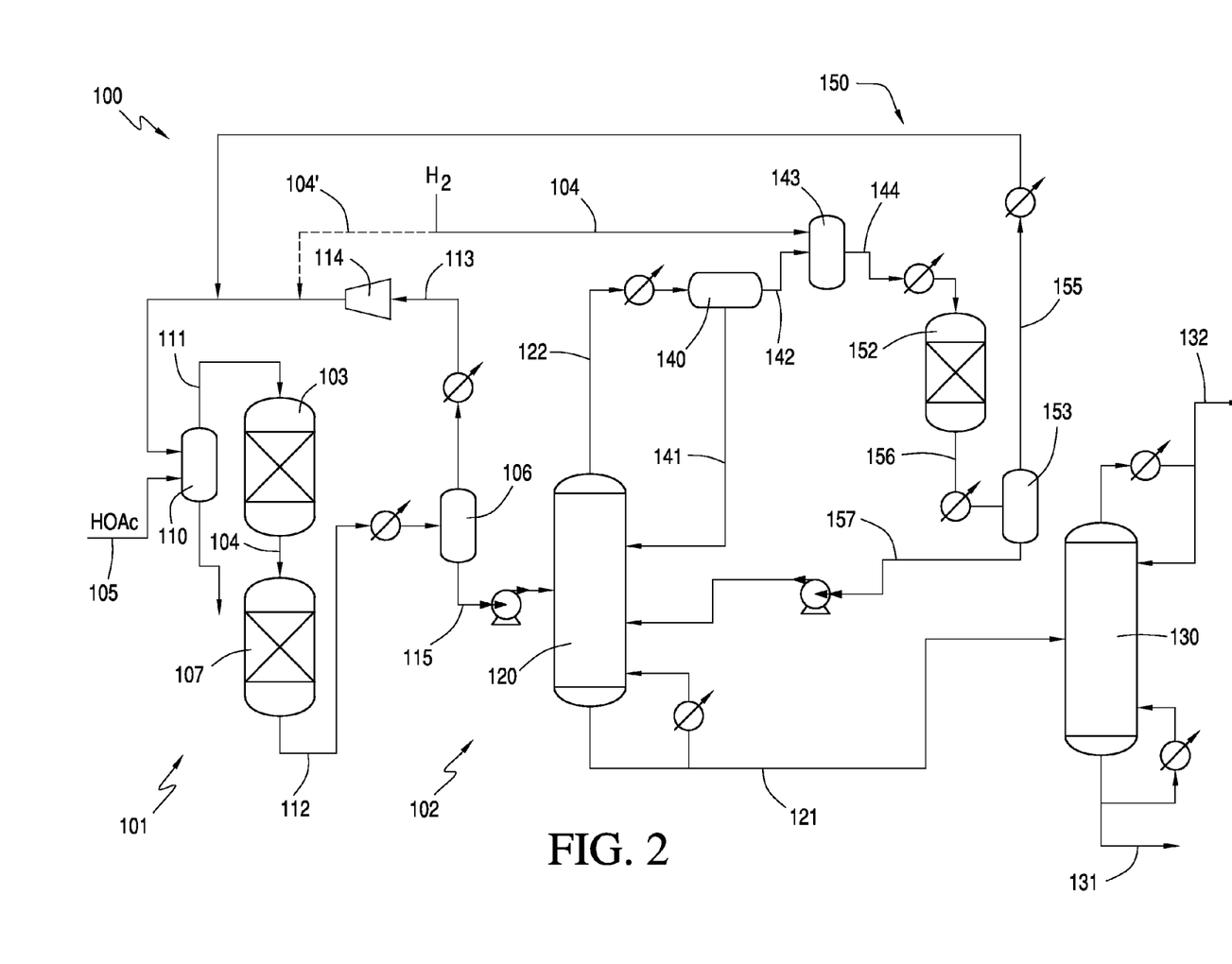
FIG. 2 is a schematic diagram of an ethanol production system in accordance with another embodiment of the present invention.

FIGS. 1 and 2 show a hydrogenation system 100 suitable for the hydrogenation of acetic acid, the hydrogenolysis of ethyl acetate and separating ethanol from the crude reaction mixture according to one embodiment of the invention. System 100 comprises reaction zone 101, separation zone 102, and hydrogenolysis zone 150. Reaction zone 101 in FIG. 1 comprises reactor 103, acetic acid feed line 105, and vaporizer 110. Reaction zone 101 in FIG. 2 additionally comprises reaction product 104 and esterification reactor 107. Separation zone 102 comprises separator 106, first column 120, second column 130, and decanter 140. Hydrogenolysis zone 150 comprises hydrogen feed line 104, secondary reactor 152, flasher 153 and vaporizer 154.

As shown in FIG. 1, hydrogen is preferably fed directly to hydrogenolysis zone 150 via line 104. In embodiments of the present invention there is substantially no hydrogen in the organic phase from the separation zone 102 that is fed to the hydrogenolysis zone 150 and fresh hydrogen via line 104 is preferably added to hydrogenolysis zone 150. The excess hydrogen from hydrogenolysis zone 150 may be flashed and fed to the reaction zone 101 via line 155. In one embodiment, the hydrogen fed to hydrogenation reactor 103 is fed without increasing the pressure from the feed source. In addition, the secondary reactor 152 preferably does not have a gas recycle loop. Optionally, hydrogen may also be fed directly to reaction zone 101 via line 104'. In preferred embodiments, hydrogen from lines 104' and/or 155 may be added downstream of compressor 114. Hydrogen from the reaction zone 101 in line 113 may also be combined with the hydrogen from line 104' and/or 155.

In other embodiments, there may be separate hydrogen sources for the hydrogenation reactor 103 and secondary reactor 152.

In one embodiment, hydrogen may be fed to the reaction zone 101 via line 104' and the unreacted hydrogen is flashed and separated from the crude product and fed to the secondary reactor 152.

Hydrogen, either fed directly from line 104', indirectly from line 155 or a combination of both, and acetic acid via line 105 may be fed to a vaporizer 110 in reaction zone 101. In one embodiment, hydrogen and acetic acid may be combined and jointly fed to the vaporizer 110, e.g., in one stream containing both hydrogen and acetic acid. Vaporizer 110 generates a vapor feed stream in line 111 that is directed to reactor 103. The temperature of the vapor feed stream in line 111 is preferably from 100° C. to 350° C., e.g., from 120° C. to 310° C. or from 150° C. to 300° C. Any feed that is not vaporized is removed from vaporizer 110, as shown, and may be recycled or discarded. In addition, although FIG. 1 represents line 111 being directed to the top of reactor 103, line 111 may be directed to the side, upper portion, or bottom of reactor 103. Further modifications and additional components to reaction zone 101 are described below.

Reactor 103 contains the catalyst that is used in the hydrogenation of the carboxylic acid, preferably acetic acid, to form ethyl acetate. In one embodiment, one or more guard beds (not shown) may be used upstream of the reactor, optionally upstream of vaporizer 110, to protect the catalyst from poisons or undesirable impurities contained in the feed or return/recycle streams. Such guard beds may be employed in the vapor or liquid streams. Suitable guard bed materials are known in the art and include, for example, carbon, silica, alumina, ceramic, or resins. In one aspect, the guard bed media is functionalized, e.g., silver functionalized, to trap particular species such as sulfur or halogens. During the hydrogenation process, a crude product is withdrawn, preferably continuously, from reactor 103 via line 112.

The crude product may be condensed and fed to separator 106, which, in turn, provides a vapor stream 113 and a liquid stream 115. Suitable separators 106 include one or more flashers or knockout pots. The separator 106 may operate at a temperature from 20° C. to 250° C., e.g., from 30° C. to 225° C. or from 60° C. to 200° C. The pressure of separator 106 may be from 50 kPa to 2000 kPa, e.g., from 75 kPa to 1500 kPa or from 100 kPa to 1000 kPa. Optionally, the crude product in line 112 may pass through one or more membranes, not shown, to separate hydrogen and/or other non-condensable gases therefrom.

The vapor stream exiting the separator 106 may comprise hydrogen and hydrocarbons, which may be purged and/or returned to reaction zone 101 via line 113. As shown, the returned portion of the vapor stream 113 may be combined with the hydrogen feed from lines 104' and/or 155 downstream of compressor 114 and co-fed to vaporizer 110. In some embodiments, the returned vapor stream 113 may be compressed before being combined with the hydrogen feed.

The liquid from separator 106 is withdrawn and pumped via line 115 to the side of first column 120, also referred to as the combined column. In one embodiment, the contents of line 115 are substantially similar to the crude product obtained from the reactor, except that the composition has substantially no hydrogen, carbon dioxide, methane or ethane, which are removed by separator 106. Exemplary components of liquid in line 115 are provided in Table 2. Liquid stream 115 may contain other components not specifically listed in Table 2.

TABLE 2

COLUMN FEED COMPOSITION
(Liquid Stream 115)

|  | Conc. (wt. %) | Conc. (wt. %) | Conc. (wt. %) |
|---|---|---|---|
| Ethanol | 5 to 40 | 5 to 35 | 5 to 30 |
| Acetic Acid | <10 | <5 | <1 |
| Water | 5 to 35 | 5 to 30 | 10 to 30 |
| Ethyl Acetate | 40 to 95 | 45 to 90 | 50 to 85 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout the present application are preferably not present and if present may be present in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, the liquid stream, e.g., line 115, may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

Liquid stream 115 is introduced in the middle of combined column 120. In combined column 120, a weight majority of the ethanol, water, acetic acid, and other heavy components, if present, are removed from liquid stream 115 and are withdrawn, preferably continuously, as residue in line 121. In one embodiment, the first column 120 may be an extractive distillation column. In such embodiments, an extraction agent, such as for example water, may be added to first column 120. In one embodiment, the extraction agent may be water obtained from the aqueous phase in line 141. In other embodiments, the extraction agent may be obtained from an external source or from an internal return/recycle line from one or more of the other columns, such as water stream 131.

Other suitable extractive agents may include, for example, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N-dimethyl-1,3-propanediamine, N,N'-dimethylethylenediamine, diethylene triamine, hexamethylene diamine and 1,3-diaminopentane, an alkylated thiopene, dodecane, tridecane, tetradecane, chlorinated paraffins, or a combination thereof.

The columns shown in the figures may comprise any distillation column capable of performing the desired separation and/or purification. Each column preferably comprises a tray column having from 1 to 150 trays, e.g., from 10 to 100, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in FIG. 1. As shown in FIG. 1, heat may be supplied to the base of each column or to a circulating bottoms stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and flasher are shown, additional reactors, flashers, condensers, heating elements, and other components may be used in embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in any of the columns may vary. As a practical matter, pressures from 10 kPa to 3000 kPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, that the temperature at a given location in an operating distillation column is dependent on the composition of the material at that location and the pressure of column. In addition, feed rates may vary depending on the size of the production process and, if described, may be generically referred to in terms of feed weight ratios.

When combined column 120 is operated under about 170 kPa, the temperature of the residue exiting in line 181 preferably is from 70° C. to 155° C., e.g., from 90° C. to 130° C. or from 100° C. to 110° C. The base of combined column 120 may be maintained at a relatively low temperature by withdrawing a residue stream comprising ethanol, water, and acetic acid, thereby providing an energy efficiency advantage. The temperature of the distillate exiting in line 182 preferably at 170 kPa is from 75° C. to 100° C., e.g., from 75° C. to 83° C. or from 81° C. to 84° C. In some embodiments, the pressure of combined column 120 may range from 0.1 kPa to 510 kPa, e.g., from 1 kPa to 475 kPa or from 1 kPa to 375 kPa. Exemplary components of the distillate and residue compositions for combined column 120 are provided in Table 3 below. It should also be understood that the overhead and residue may also contain other components, not listed in Table 3. Note that these compositions may change depending on acetic acid conversion, the operation of the column, and whether a majority of the water is removed in the residue. It should be understood that the overhead and residue may also contain other components, not listed, such as components in the feed. For convenience, the overhead and residue of the first column may also be referred to as the "first overhead" or "first residue." The overheads or residues of the other columns may also be referred to with similar numeric modifiers (second, third, etc.) in order to distinguish them from one another, but such modifiers should not be construed as requiring any particular separation order.

TABLE 3

COMBINED COLUMN 120 (FIG. 1)

| | Conc. (wt. %) | Conc. (wt. %) | Conc. (wt. %) |
|---|---|---|---|
| Overhead | | | |
| Ethyl Acetate | 50 to 99.9 | 55 to 97 | 60 to 95 |
| Acetaldehyde | <10 | 0.0001 to 5 | 0.001 to 1.5 |
| Acetal | <5 | 0.0001 to 3 | 0.001 to 1.5 |
| Acetone | <0.05 | 0.001 to 0.03 | 0.01 to 0.025 |
| Ethanol | <30 | 0.0001 to 5 | 0.001 to 0.5 |
| Water | 0.1 to 30 | 1 to 15 | 2 to 10 |
| Acetic Acid | <2 | <0.1 | <0.05 |
| Residue | | | |
| Acetic Acid | 0.01 to 35 | 0.1 to 30 | 0.2 to 25 |
| Water | 25 to 80 | 30 to 75 | 35 to 70 |
| Ethanol | 10 to 75 | 15 to 70 | 20 to 65 |

In an embodiment of the present invention, combined column 120 may be operated at a temperature where most of the water, ethanol, and acetic acid are removed from the residue stream and only a small amount of ethanol and water is collected in the distillate stream due to the formation of binary and tertiary azeotropes. The mass flow of water in the residue in line 121 to water in the distillate in line 122 may be greater than 2:1, e.g., greater than 10:1. The mass flow of ethanol in the residue to ethanol in the distillate may be greater than 10:1, e.g., greater than 50:1.

The amount of acetic acid in the first residue may vary depending primarily on the conversion in reaction zone 101. In one embodiment, when the conversion is high, e.g., greater than 90%, the amount of acetic acid in the first residue may be less than 10 wt. %, e.g., less than 5 wt. % or less than 2 wt. %. In other embodiments, when the conversion is lower, e.g., less than 90%, the amount of acetic acid in the first residue may be greater than 10 wt. %.

The overhead preferably is substantially free of acetic acid, e.g., comprising less than 1000 wppm, less than 500 wppm or less than 100 wppm acetic acid. In general, the overhead in line 122 is condensed and collected in an overhead receiver, e.g., decanter, 140 to form an organic phase 142 comprising ethyl acetate and an aqueous phase 141 comprising water and ethanol. Organic phase 142 is fed to a hydrogenolysis zone 150. The crude reaction product of the secondary reactor 152 is continuously withdrawn via line 156 and separated into a liquid stream in line 157 and a vapor stream 155. The liquid stream in line 157 may be fed to first column 120.

First overhead in line 122 may be biphasically separated in an overhead decanter 140. Condensing the first overhead may cause phase separation into a low density or lighter phase that is an organic phase rich in ethyl acetate and a more dense or heavier phase that is an aqueous phase rich in water. To further effectuate phasing, decanter 140 may be maintained a temperature from 0 to 40° C. In another embodiment, water may be added to decanter 140 to enhance phase separation. The water added to decanter 140 extracts ethanol from the organic phase thereby decreasing the water concentration in the organic phase. The water may be supplied from within the process, e.g., from line 131, or from an external source. In other embodiments, the first overhead may have molar ratio of ethanol to ethyl acetate from 1:5 to 1:1.1, e.g., from 1:3 to 1:1.4, or from 1:2 to 1:1.25. A suitable molar ratio of ethanol to ethyl acetate to provide phasing may be 1.1:1.25. The low molar ratio of ethanol to ethyl acetate may also affect phasing. In addition, the low molar ratio of ethanol may also reduce the ethanol concentration in the organic phase and thus also reduce the water concentration in the organic phase.

Exemplary organic phase and aqueous phase compositions are provided in Table 4 below. It is preferred that each phase contains very low concentrations of acetic acid, e.g., less than 600 wppm, e.g., less than 200 wppm or less than 50 wppm. In one embodiment, the organic phase comprises less than 6 wt. % ethanol and less than 5 wt. % water.

TABLE 4

OVERHEAD DECANTER 140

| | Conc. (wt. %) | Conc. (wt. %) | Conc. (wt. %) |
|---|---|---|---|
| Organic Phase | | | |
| Ethyl Acetate | 60 to 99.5 | 60 to 97 | 75 to 95 |
| Water | 0.01 to 10 | 0.5 to 8 | 0.5 to 5 |
| Ethanol | 0.01 to 10 | 0.5 to 6 | 0.5 to 5 |
| Diethyl acetal | <1 | <0.1 | <0.05 |
| $C_3$+ alcohols | <1 | <0.1 | <0.05 |
| Aqueous Phase | | | |
| Water | 60 to 99.5 | 60 to 97 | 75 to 95 |
| Ethyl Acetate | 0.01 to 30 | 0.5 to 25 | 1 to 15 |
| Ethanol | 0.01 to 20 | 0.1 to 15 | 0.5 to 10 |
| Diethyl acetal | <0.1 | <0.01 | <0.001 |
| $C_3$+ alcohols | <1 | <0.1 | <0.05 |

In some embodiments, a portion of the organic phase may also be refluxed. The remaining portion of organic phase in line 142, or an aliquot portion thereof, may be directly fed as the ester feed stream to hydrogenolysis zone 150. In some embodiments, it may be preferred to preheat the organic phase directly fed to hydrogenolysis zone 150.

In FIG. 1, at least a portion of the organic phase in line 142 and hydrogen feed stream 104 are fed to vaporizer 143 to form a gaseous portion of the organic phase in line 144. This gaseous portion of the organic phase is directed to hydrogenolysis zone 150. In addition, gaseous portion in line 144 may also be pre-heated before being fed to hydrogenolysis zone 150. The gaseous portion and hydrogen in line 144 may be preheated to a temperature of at least 150° C., e.g., at least 200° C. or at least 250° C. before being fed to secondary reactor 152, provided that the feed, i.e., gaseous portion 144, remains in the vapor phase and above the dew point.

The secondary reactor 152 preferably comprises a hydrogenolysis catalyst. The reactants, namely the ethyl acetate in the gaseous portion of the organic phase, react in the presence of hydrogen and the catalyst to form ethanol. Suitable hydrogenolysis catalysts include copper support on silica or copper oxide supported on magnesia-silica, Raney copper catalysts, Group VIII supported catalysts, and catalysts as described above with respect to the hydrogenation reaction. Further catalysts are described in U.S. Pat. No. 5,198,592, and Claus, et al., "Selective Hydrogenolysis of methyl and ethyl acetate in the gas phase on copper and supported Group VIII metal catalysts," Applied Catalysts A: General, Vol. 79 (1991) pages 1-18, which are incorporated herein by reference.

In one embodiment, a heterogeneous catalyst is used in secondary reactor 152. The catalyst may be a copper-based catalyst. Copper-based catalyst may comprise copper chromite, copper and zinc, and/or copper-zinc-oxide. Other copper-based catalyst may include an $MgO-SiO_2$ support that is impregnated with copper. Mixed copper oxide based catalyst may include copper and a second metal selected from zinc, zirconium, manganese, and/or oxides thereof. In some embodiments, aluminum oxide may also be present in the catalyst. The presence of aluminum oxide is believed to increase the heavy alcohol, and/or ketone concentrations during the reduction of ethyl acetate due to the presence of acidic sites. In those embodiments, the catalyst may comprise a basic component, such as magnesium or calcium, to reduce the acidic sites or the aluminum oxide concentration may be very low, e.g., less than 0.1 wt. %. In some embodiments, the catalyst may be substantially free of aluminum oxide.

A suitable copper-based catalyst may comprises from 30 to 70 wt. % copper oxide, 15 to 45 wt. % zinc oxide, and/or 0.1 to 20 wt. % aluminum oxide. More preferably, a copper-based catalyst may comprises from 55 to 65 wt. % copper oxide, 25 to 35 wt. % zinc oxide, and/or 5 to 15 wt. % aluminum oxide. Preferably, the copper-based catalyst is supported on zinc oxide and preferably comprises from 20 to 40 wt. % of copper, in terms of the metal content.

In other embodiments, the catalyst employed in secondary reactor 152 may be a Group VIII-based catalyst. Group VIII-based catalyst may comprise a Group VIII metal selected from the group consisting of iron, ruthenium, osmium, cobalt, rhodium, iridium, nickel, palladium, and platinum. In addition, there may be one or more secondary promoter metals selected from the group consisting of zinc, cobalt, tin, germanium, lead, rhenium, tungsten, molybdenum. Group VIII-based catalysts may advantageously be supported on any suitable support known to those skilled in the art; non-limiting examples of such supports include carbon, silica, titania, clays, aluminas, zinc oxide, zirconia and mixed oxides. Preferably, the palladium based catalyst is supported on carbon. In addition, the Group VIII-based catalyst may be supported on any suitable support, such as silica, silica-alumina, calcium metasiciliate, carbon, titania, clays, aluminas, zinc oxide, zirconia, and mixed metal oxides. For example, palladium based catalysts may be supported on carbon.

The reduction of ethyl acetate to produce ethanol, e.g., in secondary reactor 152, is typically conducted at elevated temperatures from 125° C. to 350° C., e.g., from 180° C. to 345° C., from 225° C. to 310° C., or from 290° C. to 305° C. Reaction temperatures greater than 240° C., or greater than 260° C., may increase conversion of ethyl acetate. Although not bound by theory, it is believed that reduced temperatures in the hydrogenolysis reactor of less than 275° C. may suppress the formation of heavy impurities such as alcohols and/or ketones. The pressure in the hydrogenolysis reactor may operate under high pressure of greater than 1000 kPa, e.g., greater than 3,000 kPa or greater than 5,000 kPa. In terms of ranges the pressure in the hydrogenolysis reaction may be from 700 to 8,500 kPa, e.g., from 1,500 to 7,000 kPa, or from 2,000 to 6,500 kPa. Pressure greater than 2,500 kPa may be more favorable for improving ethanol productivity and/or selectivity. The reactants may be fed to hydrogenolysis reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 20,000 $hr^{-1}$, e.g., from 1000 $hr^{-1}$ to 10,000 $hr^{-1}$, or from 2000 $hr^{-1}$ to 7,000 $hr^{-1}$.

The secondary reactor 152 is preferably operated under conditions effective to convert at least 40% of the ethyl acetate to ethanol, e.g., at least 80% or at least 90%. The hydrogenolysis reaction may be conducted with excess molar amounts of hydrogen and preferably the molar ratio of hydrogen to ethyl acetate is greater than 10:1, e.g., greater than 15:1, or greater than 20:1. In one preferred embodiment, the molar ratio is about 25:1. The excess hydrogen may be removed and fed to the hydrogenation reactor 103.

The secondary crude reaction product, also referred to as the hydrogenolysis product of the organic phase, is continuously withdrawn via line 156. In one embodiment, the secondary crude reaction product comprises at least 5% less ethyl acetate than the gaseous portion of the organic phase in via 144, e.g., at least 75% less ethyl acetate or at least 90% less ethyl acetate. In another embodiment, the secondary crude reaction product comprises at least 5% more ethanol than the gaseous portion of the organic phase in via 144, e.g., at least 10% more ethanol, or at least 25% more ethanol. Other components, such as water, acetaldehyde, and other impurities may be present in the secondary crude product in minor amounts.

The secondary crude product may be condensed and fed to separator 153, which, in turn, provides a vapor stream and a liquid stream. The separator 153, e.g., a flasher or knock-out pot, in one embodiment operates at a temperature of from 50° C. to 500° C., e.g., from 70° C. to 400° C. or from 100° C. to 350° C. In one embodiment, the pressure of separator 106 is from 50 kPa to 2000 kPa, e.g., from 75 kPa to 1500 kPa, or from 100 kPa to 1000 kPa.

The vapor stream exiting the separator 153 may comprise hydrogen and hydrocarbons, which may be purged and/or returned to reaction zone 101 via line 155. As shown in FIG. 1, the returned portion of the vapor stream in line 155 is combined with the hydrogen vapor stream of line 113 that passes through compressor 114.

The liquid stream exiting the separator 153 comprises ethanol and is preferably returned to the separation zone 102 via line 157. As shown in FIG. 1, the liquid stream in line 157 is returned to combined column 120, preferably below the inlet for liquid stream in line 115. Returning liquid stream in line 157 below the inlet of liquid stream 115 may further concentration ethanol in the line 121. In other embodiments, when liquid stream in line 157 is deficient in ethyl acetate, a portion of the liquid stream in line 157 may be combined with the residue in line 121.

To recover ethanol, the residue in line 121 may be further separated in a second column 130, also referred to as a "product column." The first residue in line 121 is introduced to second column 130 preferably in the top part of column 130, e.g., top half or top third. Second column 130 yields a water stream in line 131 comprising acetic acid and water, and a ethanol stream in line 132 comprising ethanol. Second column 130 may be a tray column or packed column. In one embodiment, second column 130 is a tray column having from 5 to 150 trays, e.g., from 15 to 50 trays or from 20 to 45 trays. Although the temperature and pressure of second column 130 may vary, when at atmospheric pressure the temperature of the water stream exiting in line 131 preferably is from 95° C. to 130° C., e.g., from 100° C. to 125° C. or from 110° C. to 120° C. The temperature of the ethanol stream exiting in line 132 preferably is from 60° C. to 105° C., e.g., from 75° C. to 100° C. or from 80° C. to 100° C. The pressure of second column 130 may range from 0.1 kPa to 510 kPa, e.g., from 1 kPa to 475 kPa or from 1 kPa to 375 kPa.

Exemplary components for the overhead and residue compositions for second column 130 are provided in Table 5 below. It should be understood that the overhead and residue may also contain other components, not listed in Table 5.

TABLE 5

SECOND COLUMN 130 (FIG. 1)

|  | Conc. (wt. %) | Conc. (wt. %) | Conc. (wt. %) |
|---|---|---|---|
| Distillate |  |  |  |
| Ethanol | 75 to 96 | 80 to 96 | 85 to 96 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |
| Residue |  |  |  |
| Water | 75 to 99.9 | 80 to 99 | 90 to 99 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <10 | 0.001 to 5 | 0.005 to 1 |

The weight ratio of ethanol in the ethanol stream in line 132 to ethanol in the water stream in line 131 preferably is at least 35:1. In one embodiment, the weight ratio of water in the water stream 131 to water in the ethanol stream 132 is greater than 2:1, e.g., greater than 4:1 or greater than 6:1. In addition, the weight ratio of acetic acid in the water stream 131 to acetic acid in the ethanol stream 132 preferably is greater than 10:1, e.g., greater than 15:1 or greater than 20:1. Preferably, the ethanol stream in line 132 is substantially free of acetic acid and may only contain, if any, trace amounts of acetic acid. Preferably, the ethanol stream in line 132 contains substantially no ethyl acetate.

The remaining water from the ethanol stream in line 132 may be removed in further embodiments of the present invention. Depending on the water concentration, the ethanol product may be derived from the ethanol stream in line 132. Some applications, such as industrial ethanol applications, may tolerate water in the ethanol product, while other applications, such as fuel applications, may require an anhydrous ethanol. The amount of water in the ethanol stream of line 132 may be closer to the azeotropic amount of water, e.g., at least 4 wt. %, preferably less than 20 wt. %, e.g., less than 12 wt. % or less than 7.5 wt. %. Water may be removed from the ethanol stream in line 132 using several different separation techniques as described herein. Particularly preferred techniques include the use of distillation column, membranes, adsorption units, and combinations thereof.

Optionally, a substantial portion of the water from the crude product, e.g., from 30 to 90 wt. %, may be removed in residue in line 121. Depending on the composition, the residue stream may be: (i) entirely or partially recycled to the hydrogenation reactor, (ii) separated into acid and water streams, (iii) treated with a solvent in a weak acid recovery process, (iv) reacted with an alcohol to consume the unreacted acetic acid, or (v) disposed to a waste water treatment facility.

In another embodiment, unreacted acetic acid, water, and other heavy components, if present, are removed from the composition in line 115 and are withdrawn, preferably continuously, as the residue of column 120. In some embodiments, especially with higher conversions of acetic acid of at least 80%, or at least 90%, it may be beneficial to remove a majority of water in the residue of column 120 along with substantially all of the acetic acid. Residue stream 121 may be recycled to reaction zone 101. In addition, a portion of the water in residue stream 121 may be separated and purged with the acid rich portion being returned to reaction zone 101. In other embodiments, the residue stream 121 may be a dilute acid stream that may be treated in a weak acid recovery system or sent to a reactive distillation column to convert the acid to esters.

As discussed above, in one embodiment, a substantial portion of the water from the liquid stream in line 115 may be separated into the residue in line 121. As a result the water concentrations in Table 3 for the residue would be higher, e.g. up to 90 wt. %, or up to 75 wt. %. Particularly at high conversions, the residue of the first column 120 may comprise a significantly greater concentration of water than is indicated in Table 3. In other embodiments, the residue stream 121 may be a dilute acid stream that may be treated in a weak acid recovery system or sent to a reactive distillation column to convert the acid to esters.

FIG. 2 shows a similar reaction zone to FIG. 1, with the addition of an esterification reactor 107. When a reaction product 104 exits hydrogenation reactor 103, the reaction product may be deficient in ethyl acetate. In addition, the esterification reactor 107 may reduce the acetic acid concentration if the acetic acid conversion is too low in the hydrogenation reactor 103. The reaction product is then fed to esterification reactor 107 to produce sufficient ethyl acetate to allow the overhead in line 122 to be biphasically separated to form an organic phase and an aqueous phase. Although FIG. 2 shows vapor phase esterification, the liquid stream in line 115 may be fed to the esterification reactor, resulting in liquid phase esterification.

The esterification reaction preferably is carried out in the vapor phase at a reaction temperature that ranges from 20° C. to 250° C., e.g., from 50° C. to 225° C., or from 100° C. to 200° C. In one embodiment, the esterification reaction is conducted at a temperature that is less than the hydrogenation reaction temperature. The pressure in the esterification reactor may vary depending on the hydrogenation reaction pressure and generally ranges from 10 kPa to 3000 kPa, e.g., from 50 kPa to 2300 kPa, or from 100 kPa to 1500 kPa. Preferably the pressure of esterification reactor is similar to the pressure of the hydrogenation reactor.

Acid-catalyzed esterification reactions may be used with some embodiments of the present invention. The catalyst should be thermally stable at reaction temperatures. Suitable catalysts may be solid acid catalysts comprising an ion exchange resin, zeolites, Lewis acid, metal oxides, inorganic salts and hydrates thereof, and heteropoly acid and salts thereof. Silica gel, aluminum oxide, and aluminum phosphate are also suitable catalysts. Acid catalysts include, but are not limited to, sulfuric acid, and tosic acid. In addition, Lewis acids may also be used as esterification catalysts, such as scandium(III) or lanthanide(III) triflates, hafnium(IV) or zirconium(IV) salts, and diarylammonium arenesulfonates. The catalyst may also include sulfonated (sulphonic acid) ion-exchange resins (e.g., gel-type and macroporous sulfonated styrene-divinyl benzene IERs), sulfonated polysiloxane resins, sulfonated perfluorinated (e.g., sulfonated poly-perfluoroethylene), or sulfonated zirconia.

The ethanol composition obtained by the processes of the present invention may be an industrial grade ethanol comprising from 75 to 96 wt. % ethanol, e.g., from 80 to 96 wt. % or from 85 to 96 wt. % ethanol, based on the total weight of the finished ethanol composition. Exemplary finished ethanol compositional ranges are provided below in Table 6.

TABLE 6

FINISHED ETHANOL COMPOSITIONS

| Component | Conc. (wt. %) | Conc. (wt. %) | Conc. (wt. %) |
| --- | --- | --- | --- |
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be higher than indicated in Table 7, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including applications as fuels, solvents, chemical feedstocks, pharmaceutical products, cleansers, sanitizers, hydrogen transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882, 244 and zeolite Y in U.S. Pat. No. 3,130,007, the entireties of which are hereby incorporated herein by reference.

While the invention has been described in detail, modifications within the spirit and scope of the invention will be readily apparent to those of skill in the art. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing ethanol, comprising:
   hydrogenating acetic acid in the presence of a catalyst under conditions effective to produce a crude product comprising from 0 to 10 wt. % acetic acid, from 40 to 95 wt. % ethyl acetate and from 5 to 40 wt. % ethanol, wherein ethyl acetate is present in a greater weight amount than ethanol;
   introducing at least a portion of the crude product at an inlet to a distillation column and obtaining an overhead that is condensed and collected;
   maintaining conditions to biphasically separate the condensed and collected overhead into an organic phase comprising ethyl acetate and an aqueous phase;
   feeding the aqueous phase to the distillation column above the inlet of the crude product to extract ethanol from ethyl acetate;
   feeding a secondary crude product formed by hydrogenolyzing at least a portion of the organic phase to the distillation column below the inlet of the crude product; and
   recovering ethanol from a residue of the distillation column.

2. The process of claim 1, wherein the catalyst comprises a first metal selected from the group consisting of copper, iron, cobalt, nickel, ruthenium, rhodium, palladium, osmium, iridium, platinum, titanium, zinc, and chromium, and a second metal selected from the group consisting of copper, tin, chromium, iron, cobalt, vanadium, palladium, platinum, lanthanum, cerium, manganese, ruthenium, gold and nickel, wherein the second metal is different than the first metal; and further wherein the catalyst comprises a support and at least one support modifier selected from the group consisting of oxides of Group IVB metals, oxides of Group VB metals, oxides of Group VIB metals, iron oxides, aluminum oxides, and mixtures thereof.

3. The process of claim 1, wherein the selectivity of acetic acid to ethyl acetate is at least 50%.

4. The process of claim 1, wherein the organic phase comprises at least 90 wt. % ethyl acetate.

5. The process of claim 1, wherein the distillation column is an extractive distillation column.

6. The process of claim 1, wherein the residue is separated in a second distillation column to form an ethanol stream and a water stream.

7. The process of claim 6, further comprising the step of:
   combining the secondary crude product with the residue.

8. The process of claim 1, wherein the secondary crude product comprises at least 5% more ethanol than the at least a portion of the organic phase fed to a hydrogenolysis reactor.

9. The process of claim 1, wherein the at least a portion of the organic phase is reacted in the presence of a hydrogenolysis catalyst.

10. The process of claim 1, further comprising:
    feeding hydrogen to a hydrogenolysis reactor to form a hydrogenolysis product of the organic phase;
    feeding at least a portion of the secondary crude product to a flasher to generate a vapor stream comprising hydrogen; and
    introducing the vapor stream to a hydrogenation reactor for hydrogenating the acetic acid.

11. The process of claim 10, further comprising introducing at least a portion of the vapor stream to the hydrogenolysis reactor.

12. A process for producing ethanol, comprising:
    hydrogenating acetic acid in the presence of a catalyst under conditions effective to produce a crude product comprising from 0 to 10 wt. % acetic acid, from 40 to 95 wt. % ethyl acetate and from 5 to 40 wt. % ethanol, wherein ethyl acetate is present in a greater weight amount than ethanol;
    separating at least a portion of the first crude product in a distillation column to form an overhead comprising ethyl acetate and water and a residue comprising ethanol and water;
    biphasically separating the overhead to form an organic phase comprising ethyl acetate and an aqueous phase comprising water;
    reacting at least a portion of the organic phase in the presence of hydrogen to form a secondary crude product; and
    combining the secondary crude product with the residue to recover ethanol.

13. The process of claim 12, wherein the aqueous phase is returned to the distillation column.

14. The process of claim 12, wherein the organic phase comprises at least 90 wt. % ethyl acetate.

15. The process of claim 12, wherein the distillation column is an extractive distillation column.

16. The process of claim 12, wherein the residue is separated in a second distillation column to form an ethanol stream and a water stream.

17. The process of claim 12, wherein the secondary crude product comprises at least 5% more ethanol than the at least a portion of the organic phase fed to the second reactor.

18. The process of claim 12, wherein the at least a portion of the organic phase is reacted in the presence of a hydrogenolysis catalyst.

19. The process of claim 18, wherein the hydrogenolysis catalyst comprises a copper-based catalyst.

20. The process of claim 1, wherein the residue comprises from 0.01 to 35 wt. % acetic acid, from 25 to 80 wt. % water, and from 10 to 75 wt. % ethanol.

* * * * *